US008119837B2

(12) United States Patent
Azemi et al.

(10) Patent No.: US 8,119,837 B2
(45) Date of Patent: Feb. 21, 2012

(54) PROCESS FOR PRODUCING METHIONINE

(75) Inventors: Takushi Azemi, Ehime (JP); Yoshiyuki Koizumi, Ehime (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 149 days.

(21) Appl. No.: 12/613,580

(22) Filed: Nov. 6, 2009

(65) Prior Publication Data

US 2010/0121104 A1    May 13, 2010

(30) Foreign Application Priority Data

Nov. 7, 2008 (JP) ................................. 2008-287062

(51) Int. Cl.
*C07C 323/22* (2006.01)
(52) U.S. Cl. ....................................................... 562/559
(58) Field of Classification Search ........................ None
See application file for complete search history.

(56) References Cited

U.S. PATENT DOCUMENTS

| 5,945,563 A | 8/1999 | Imi et al. |
| 2007/0246129 A1 | 10/2007 | Onishi |

FOREIGN PATENT DOCUMENTS

| EP | 1 849 769 A2 | 10/2007 |
| EP | 1 975 154 A1 | 10/2008 |
| JP | 10-182593 A | 7/1998 |
| JP | 11-217370 A | 8/1999 |
| JP | 2002-105048 A | 4/2002 |
| JP | 2002-114758 A | 4/2002 |
| JP | 2003-104958 A | 4/2003 |
| JP | 2003-104959 A | 4/2003 |
| JP | 2003-104960 A | 4/2003 |
| JP | 2003-119557 A | 4/2003 |
| JP | 2005187828 A | 7/2005 |
| JP | 2007-314507 A | 12/2007 |

OTHER PUBLICATIONS

Database CA [Online] Chemical Abstracts Service, Columbus, Ohio, US, Yoshihisa et al., Method for corrosion prevention of treatment equipment for wastewater containing sulfur organic compound, retreived from STN Database accession No. 143:118572.
European Search Report, dated Mar. 26, 2010.
Search Report and Written Opinion issued on Nov. 11, 2010 in Singapore Appln. Ser. No. 200907354-5.
HU Written Opinion issued Aug. 10, 2011 from the Hungarian Intellectual Property Office in counterpart SG Application No. 200907354-5.

*Primary Examiner* — Paul A Zucker
(74) *Attorney, Agent, or Firm* — Panitch Schwarze Belisario & Nadel LLP

(57) ABSTRACT

A process for producing methionine, while corrosion of a pipe and a reaction vessel is well inhibited, is provided including the following steps (1) to (3), wherein a content of thiols in 3-methylthiopropanal is 500 ppm or less, based on the propanal, and a content of hydrogen sulfide in 3-methylthiopropanal is 60 ppm or less, based on the propanal; step (1) in which 3-methylthiopropanal is reacted with hydrogen cyanide in the presence of a base to give 2-hydroxy-4-methylthiobutanenitrile; step (2) in which the 2-hydroxy-4-methylthiobutanenitrile obtained in step (1) is reacted with ammonium carbonate to give 5-(β-methylmercaptoethyl) hydantoin; and step (3) in which the 5-(β-methylmercaptoethyl)hydantoin obtained in step (2) is hydrolyzed in the presence of a basic potassium compound to give methionine.

2 Claims, 1 Drawing Sheet

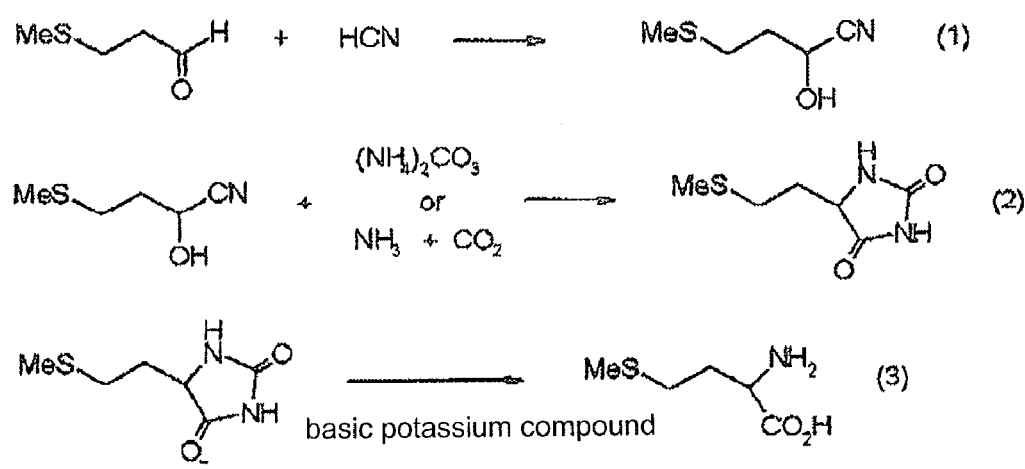

PROCESS FOR PRODUCING METHIONINE

BACKGROUND OF THE INVENTION

1. Technical Field

This application was filed claiming Paris Convention priority of Japanese Patent Application No. 2008-287062, the entire content of which is herein incorporated by reference.

The present invention relates to a process for producing methionine from 3-methylthiopropanal as a raw material by cyanohydrination, hydantoination, and hydrolysis. Methionine is useful as additives for animal feed.

2. Background Art

As a process for producing methionine, a process in which a raw material, 3-methylthiopropanal is reacted with hydrogen cyanide in the presence of a base (a cyanohydrination step); subsequently, the resulting product is reacted with ammonium carbonate (a hydantoination step); and then the resulting product is hydrolyzed to give methionine is widely known (see JP-A-2002-114758, JP-A-2002-105048, JP-A-2003-104958, JP-A-2003-104959, JP-A-2003-104960, JP-A-10-182593, JP-A-2003-119557, JP-A-11-217370 and JP-A-2007-314507).

In the production process, the step for hydrolysis of hydantoin has a defect in which pipes and reaction vessels are easily corroded, and therefore, pipes and reaction vessels made of a corrosion-inhibiting material are generally used (see JP-A-10-182593, JP-A-2003-119557, JP-A-11-217370 and JP-A-2007-314507).

SUMMARY OF THE INVENTION

However, even if the pipe and reaction vessel made of corrosion-inhibiting materials, as described above, are used in the step for hydrolysis of hydantoin, the pipe and reaction vessel may yet sometimes be corroded.

An object of the present invention is therefore to provide a process for producing methionine, which well inhibits the corrosion of a pipe and a reaction vessel.

The present inventors made intensive studies, and as a result, they proved that when 3-methylthiopropanal, a raw material, includes thiols or hydrogen sulfide as impurities in an amount more than given amounts, these impurities or their derivatives involve in corrosion of a pipe and a reaction vessel in the subsequent step for hydrolysis of hydantoin. The present inventors have further found that when 3-methylthiopropanal containing these thiols and hydrogen sulfide in decreased contents of given contents or less is used as a raw material in the cyanohydrination step, the corrosion of the pipe and reaction vessel can be well inhibited in the subsequent step for hydrolysis of hydantoin, and have completed the present invention.

That is, the present invention provides:

[1] a process for producing a methionine including the following steps (1) to (3), wherein a content of thiols in 3-methylthiopropanal is 500 ppm or less, based on the propanal, and a content of hydrogen sulfide in 3-methylthiopropanal is 60 ppm or less, based on the propanal;

step (1) in which 3-methylthiopropanal is reacted with hydrogen cyanide in the presence of a base to give 2-hydroxy-4-methylthiobutanenitrile;

step (2) in which the 2-hydroxy-4-methylthiobutanenitrile obtained in step (1) is reacted with ammonium carbonate to give 5-(β-methylmercaptoethyl) hydantoin; and step (3) in which the 5-(β-methylmercaptoethyl)hydantoin obtained in step (2) is hydrolyzed in the presence of a basic potassium compound to give methionine;

[2] the process according to [1], wherein the thiols are 3-mercaptopropanal and/or methyl mercaptan; and the like.

According to the present invention, methionine can be produced while corrosion of a pipe and a reaction vessel is well inhibited in the step for hydrolysis of hydantoin.

BRIEF DESCRIPTION OF THE SEVERAL VIEWS OF THE DRAWINGS

The foregoing summary, as well as the following detailed description of the invention, will be better understood when read in conjunction with the appended drawing. For the purpose of illustrating the invention, there are shown in the drawing embodiments which are presently preferred. It should be understood, however, that the invention is not limited to the precise arrangements and instrumentalities shown.

In the drawings:

FIG. 1 is a reaction scheme for producing methionine according to an embodiment of the invention.

DETAILED DESCRIPTION OF THE INVENTION

According to the present invention, methionine is produced by the following steps (1) to (3):

step (1) in which 3-methylthiopropanal is reacted with hydrogen cyanide in the presence of a base to give 2-hydroxy-4-methylthiobutanenitrile;

step (2) in which the 2-hydroxy-4-methylthiobutanenitrile obtained in step (1) is reacted with ammonium carbonate to give 5-(β-methylmercaptoethyl)hydantoin; and step (3) in which the 5-(β-methylmercaptoethyl)hydantoin obtained in step (2) is hydrolyzed in the presence of a basic potassium compound to give methionine.

Step (1) Cyanohydrination Step

In this step, 3-methylthiopropanal is reacted with hydrogen cyanide in the presence of a base to give 2-hydroxy-4-methylthiobutanenitrile.

It is known that 3-methylthiopropanal, which is a raw material, is produced by a reaction of methyl mercaptan with acrolein, as shown below.

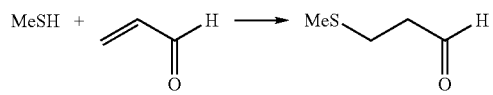

This methyl mercaptan is generally produced from hydrogen sulfide and methanol, but the resulting methyl mercaptan contains hydrogen sulfide, and therefore, when the above-mentioned reaction is performed using this mercaptan, remaining hydrogen sulfide is reacted with acrolein to produce 3-mercaptopropanal as a by-product.

Accordingly, hydrogen sulfide, 3-mercaptopropanal, and the thiols such as methyl mercaptan of the raw material remain in the obtained 3-methylthiopropanal. If the product containing such impurities is supplied to Steps (1) and (2) as it is, these impurities and their derivatives are also introduced into step (3), the step for hydrolysis of hydantoin, and they cause corrosion of a pipe and a reaction vessel. In order to inhibit such corrosion, therefore, according to the present invention, 3-methylthiopropanal containing the thiols and hydrogen sulfide with decreased contents equal to or less than given contents as the raw material in step (1).

That is, the content of thiols in 3-methylthiopropanal is 500 ppm or less, of the propanal, preferably 350 ppm or less, and the content of hydrogen sulfide in 3-methylthiopropanal is 60 ppm or less, of the propanal.

The term "thiol" refers to a compound having a mercapto group, and examples of the thiol remaining in 3-methylthiopropanal may include 3-mercaptopropanal, as described above, aldol adducts of 3-mercaptopropanal, and the like. The term "content of thiols in 3-methylthiopropanal" refers to a content of all compounds having a mercapto group in 3-methylthiopropanal.

Examples of the method for decreasing, as described above, the contents of the thiols and hydrogen sulfide in 3-methylthiopropanal to contents equal to or less than given contents may include:
(i) a method in which a content of hydrogen sulfide remaining is decreased by purifying the methyl mercaptan via distillation and the like, and then the resulting product is reacted with acrolein;
(ii) a method in which 3-methylthiopropanal is purified by distillation and the like, etc.

The thus obtained 3-methylthiopropanal is reacted with hydrogen cyanide in the presence of a base to give 2-hydroxy-4-methylthiobutanenitrile.

The amount of hydrogen cyanide used is in the range generally from 1 to 1.1 moles, per 1 mole of 3-methylthiopropanal, preferably from 1.02 to 1.08 moles. Hydrogen cyanide may be used in the state of an aqueous solution.

The reaction speed can be increased when the reaction is performed in the presence of a base. Examples of the bases include organic bases such as pyridine and triethyl amine, and inorganic bases such as potassium carbonate and ammonia. If necessary, they may be used as a mixture of the two or more kinds. The amount of the base used is in the range generally from 0.001 to 0.05 mole, and preferably from 0.003 to 0.01 mole, per 1 mole of 3-methylthiopropanal.

The reaction is preferably performed in water, whereby stability and operability of hydrogen cyanide can be improved. In order to achieve this, water may be supplied to the reaction system aside from the addition of 3-methylthiopropanal, hydrogen cyanide and the base; 3-methylthiopropanal may be used in the state of an aqueous solution; the base may be used in the state of an aqueous solution; or hydrogen cyanide may be used in the state of an aqueous solution. The amount of water used is in the range usually from 5 to 100 parts by weight, and preferably from 30 to 80 parts by weight, based on 100 parts by weight of 3-methylthiopropanal.

The reaction temperature is in the range usually from 5 to 40° C., and preferably from 10 to 30° C. The reaction time is usually in the range from 0.5 to 3 hours.

As a process for supplying 3-methylthiopropanal, hydrogen cyanide, the base and water, for example, water and hydrogen cyanide may be supplied to a mixture of 3-methylthiopropanal and the base; water may be injected into 3-methylthiopropanal along with hydrogen cyanide and the base; or the four components may be injected into the reaction system all together. When a reaction liquid is removed from the reaction system, while the four components are injected into the system all together, the reaction can be performed continuously.

After the completion of the reaction, a reaction mixture containing the resulting 2-hydroxy-4-methylthiobutanenitrile is introduced into a next step, step (2), as it is, or after a post-treatment or purification such as liquid separation, concentration or distillation, if necessary.

Step (2) Hydantoination Step

In this step, 2-hydroxy-4-methylthiobutanenitrile obtained in step (1) is reacted with ammonium carbonate to give 5-(β-methylmercaptoethyl)hydantoin.

In the hydantoination step, ammonium carbonate may be used as it is, or in the state of an aqueous solution. Also, ammonium carbonate produced from carbon dioxide gas and ammonia or produced from ammonium bicarbonate and potassium hydroxide in the reaction system or the medium may be used. The amount of ammonium carbonate used may be one mole or more per 1 mole of 2-hydroxy-4-methylthiobutanenitrile, that is an excess quantity, preferably from 1 to 4 moles.

The reaction is performed usually in water. Water may be supplied to the reaction system aside from the addition of 2-hydroxy-4-methylthiobutanenitrile and ammonium carbonate; 2-hydroxy-4-methylthiobutanenitrile may be used in the state of an aqueous solution; or ammonium carbonate may be used in the state of an aqueous solution. The amount of water used is in the range usually from 200 to 600 parts by weight, and preferably from 300 to 500 parts by weight, based on 100 parts by weight of 2-hydroxy-4-methylthiobutanenitrile.

The reaction temperature is in the range usually from 60 to 80° C., and preferably from 65 to 75° C. The reaction time is in the range usually from 2 to 4 hours.

As a process for supplying 2-hydroxy-4-methylthiobutanenitrile, ammonium carbonate and water, for example, ammonium carbonate may be supplied to an aqueous 2-hydroxy-4-methylthiobutanenitrile solution; an aqueous ammonium carbonate solution may be supplied to 2-hydroxy-4-methylthiobutanenitrile; or the three components may be injected into the reaction system all together. When a reaction liquid is removed from the reaction system, while the three components are injected into the system all together, the reaction can be performed continuously.

After the completion of the reaction, a reaction mixture containing the obtained 5-(β-methylmercaptoethyl)hydantoin is introduced into a next step, step (3), as it is, or after a post-treatment or purification such as liquid separation, concentration or distillation, if necessary.

Step (3) Hydrolysis Step

In this step, 5-(β-methylmercaptoethyl)hydantoin obtained in step (2), is hydrolyzed in the presence of a basic potassium compound to give methionine.

Examples of the basic potassium compound may include potassium hydroxide, potassium carbonate, potassium hydrogencarbonate, and the like. If necessary, they may be used as a mixture of the two or more kinds. The amount of the basic potassium compound used is usually from 2 to 10 equivalents as potassium, and preferably from 3 to 6 equivalents, per 1 equivalent of 5-(β-methylmercaptoethyl)hydantoin.

The reaction is performed in water. The amount of water used is usually from 2 to 20 times by weight based on the weight of 5-(β-methylmercaptoethyl)hydantoin.

The reaction is preferably performed under pressure, a gauge pressure of about 0.5 to 1 MPa at a temperature of about 150 to 200° C. The reaction time is usually from 10 minutes to 24 hours.

In the thus obtained hydrolysis reaction liquid, methionine exists as a potassium salt. In order to remove this methionine from the reaction liquid, carbon dioxide is introduced into the reaction liquid to conduct crystallization, and the resulting slurry is separated into precipitates and a mother liquor through filtration or decantation to give precipitated methionine as first crystals (first crystallization step).

When carbon dioxide is introduced into the reaction liquid, the carbon dioxide is absorbed in the liquid, whereby free methionine is precipitated from a potassium salt of methionine.

Carbon dioxide is preferably introduced under pressure, a gauge pressure of usually 0.1 to 1 MPa, and preferably 0.2 to 0.5 MPa.

The crystallization temperature is usually from 0 to 50° C., and preferably from 10 to 30° C. As the crystallization time, a time spent until carbon dioxide is saturated in the hydrolysis reaction liquid and methionine is sufficiently precipitated may be considered as a guideline time, and it is usually from 30 minutes to 24 hours.

The separated methionine may be washed or subjected to pH control, if necessary, which is dried thereby obtaining a product. The drying may be preferably performed under a slightly reduced pressure at a temperature of about 50 to 120° C. The drying time is usually from 10 minutes to 24 hours.

The mother liquor obtained after the separation of methionine (hereinafter referred to as "a first crystallization mother liquor") still contains methionine at a concentration equivalent to solubility, and also contains potassium hydrogencarbonate which can be recycled as the above-described basic potassium compound. Accordingly, it is desirable to recycle the first crystallization mother liquor for use in the hydrolysis reaction in the step (3). In the meantime, this mother liquor contains impurities, e.g., amino acids such as glycine and alanine, other than metionine, and a coloring component, attributed to the impurities in the stating material or the side reaction of the hydrolysis. Therefore, these impurities are brought into a hydrolysis reaction by recycling the mother liquor. To avoid this disadvantage, it is needed to recycle the first crystallization mother liquor in such an amount that these impurities are not allowed to accumulate, but not the entire amount thereof. The proportion of the first crystallization mother liquor to be recycled is usually from 50 to 90% by weight, preferably from 70 to 90% by weight, based on the entire weight of the first crystallization mother liquor.

Prior to the recycling of the first crystallization mother liquor, desirably, the same mother liquor is concentrated, and the resulting concentrate is used as a recycled solution. By this concentration, carbon dioxide is distilled off from the first crystallization mother liquor, and thus, a recycled solution with an increased basic property, advantageous for the hydrolysis reaction, can be obtained. Also, the concentration carried out at so high a temperature as from 100 to 140° C. is effective to facilitate a reaction for converting potassium hydrogencarbonate in the mother liquor, into potassium carbonate ($2KHCO_3 \rightarrow K_2CO_3 + H_2O + CO_2$), so that a recycled solution with a further increased basic property, advantageous for the hydrolysis reaction, can be obtained. While this concentration may be done under an atmospheric pressure, a reduced pressure or a raised pressure, it is effective to employ a pressurizing condition in order to carry out the concentration at a high temperature as described above. The concentration ratio is usually from 2- to 4-fold, preferably from 1.5- to 3.5-fold. In this regard, the concentration ratio means a ratio of the weight of the solution before concentration thereof to the weight of the same solution after the concentration thereof (the weight of the solution before concentration thereof/the weight of the same solution after the concentration thereof), and this term means the same, unless otherwise specified.

A portion of the first crystallization mother liquor (concentrated), which is not recycled, is crystallized so as to recover therefrom methionine and potassium hydrogencarbonate as second crystals. This crystallization is allowed to take place by introducing carbon dioxide into a mixture of the concentrated first crystallization mother liquor with a lower alcohol, and the resulting slurry is separated into a precipitate and a mother liquor by filtration or decantation, so that the precipitated methionine and potassium hydrogencarbonate are recovered as the second crystals [the second crystallization step]. In this connection, the concentrated first crystallization mother liquor may be entirely subjected to this crystallization, without recycling the same.

As the lower alcohol, any of alkyl alcohols each having a $C_{1-5}$ alkyl group is usually used. Preferable among those is an alkyl alcohol which can be admixed with water at an optional ratio, such as methyl alcohol, ethyl alcohol, n-propyl alcohol, isopropyl alcohol or t-butyl alcohol, among which isopropyl alcohol is particularly preferred. The amount of the lower alcohol to be used is usually 0.05 to 5 times, preferably 0.1 to 2 times larger in weight than the amount of the first crystallization mother liquor to be subjected to crystallization. The mixing of the first crystallization mother liquor with the lower alcohol may be done before the introduction of carbon dioxide or simultaneously with the introduction of carbon dioxide.

The first crystallization mother liquor to be subjected to the second crystallization is concentrated, as well as the first crystallization mother liquor to be recycled. By this concentration, the recovery of the second crystals can be improved. This concentration may be carried out under the same conditions as those for the concentration of the first crystallization mother liquor to be recycled; or otherwise, the entire amount of the first crystallization mother liquor may be concentrated, and then may be divided into a portion for recycling and a portion for the second crystallization.

During the concentration of the first crystallization mother liquor, the basic property of the mother liquor is enhanced, so that the free methionine formed by the conversion in the first crystallization step is again formed into a potassium salt of methihonine. Accordingly, also in the second crystallization step, carbon dioxide is introduced into a mixture of the concentrated first crystallization mother liquor with a lower alcohol to thereby convert the potassium salt of methionine into free methionine.

Preferably, the concentrated mother liquor is subjected to a heat treatment. By doing so, methionine dipeptide (a dehydro-condensation product of two methionine molecules) contained in the mother liquor is hydrolyzed to facilitate reproduction of methionine. Preferably, this heat treatment is carried out at a temperature of from about 140 to about 180° C. under a gauge pressure of 0.5 to 2 MPa, and the heat-treating time is usually from 10 minutes to 24 hours.

The introduction of carbon dioxide is done under a gauge pressure of usually from 0.1 to 1 MPa, preferably from 0.2 to 0.5 MPa, as well as that in the first crystallization step.

The crystallization temperature is usually from 0 to 50° C., preferably from 5 to 20° C. The crystallization time may be selected based on a period of time during which carbon dioxide saturates in the above-described solution mixture to sufficiently precipitate methionine and potassium hydrogencarbonate, and it is usually from 10 minutes to 24 hours.

Preferably, the recovered second crystals (a mixture of methionine and potassium hydrogencarbonate) are recycled for use in the hydrolysis reaction in the step (3). In this regard, from the viewpoint of operating efficiency, it is preferable to dissolve the second crystals in the first crystallization mother liquor to be recycled, and to recycle the resulting solution.

EXAMPLES

Next, Examples of the present invention will be illustrated. The scope of the present invention, however, is not limited to them in any way. In Examples, % and part as units of concentration and amounts are based on weight, unless otherwise specified.

Thiols and hydrogen sulfide were added to 3-methylthiopropanal containing no thiol or hydrogen sulfide (their contents being detection limit or less), which was subjected to cyanohydrination and hydantoination to prepare a raw material liquid for hydrolysis as follows:

Distillation of 200 g of 3-methylthiopropanal was performed under 20 torr at 70 to 120° C. to give 186.61 g of 3-methylthiopropanal at a purity of 98% or more. To 104.9 g of 3-methylthiopropanal was added thiols, hydrogen sulfide, sulfide or disulfide shown in Tables 1 to 5 in a predetermined amount, to which a 30% aqueous hydrogen cyanide solution (93.7 g) and a 20% aqueous potassium carbonate solution (2.764 g) were added, and cyanohydrination was performed by reacting the mixture at 15° C. for 1.5 hours to give a reaction liquid containing 2-hydroxy-4-methylthiobutanenitrile. To the reaction liquid was added a 20% aqueous ammonium carbonate solution (682.20 g), and hydantoination was performed by reacting the mixture at 70° C. for 3.5 hours to give a reaction liquid containing 5-(β-methylmercaptoethyl) hydantoin. To the reaction liquid were added 750 g of an aqueous solution containing potassium carbonate and potassium bicarbonate (K: 14.6%, $CO_2$: 10.2%) to prepare a raw material liquid for hydrolysis.

[Corrosion Test]

The raw material liquid for hydrolysis, as described above, was added to a zirconium autoclave in which a test piece was hanged, which was heated at 120° C. for 16 hours, and a corrosion condition of the test piece was visibly confirmed (evaluation: "o" and "x"). Whether or not there is a corrosive ability of a corrosion-facilitating substance was evaluated using a reduced test piece (material: DP-3) (estimation: "corrosion" or "no corrosion").

A corrosion speed of a test piece, X (mm/y) was calculated using the following equation:

$$X = (G \times 365 \times 24 \times 10)/(d \times S \times H)$$

wherein

X stands for a corrosion speed of a test piece [mm/y];
G stands for a value [(a weight (g) of a test piece before testing)−(a weight (g) of a test piece after testing)];
D stands for a density of a test piece [g/cm$^3$];
S stands for an area of a test piece [cm$^2$]; and
H stands for a testing time [h].

Corrosion speeds of a test piece of 0.02 (mm/y) or less is considered as corrosion well inhibited.

Example 1

Evaluation about Hydrogen Sulfide

To 3-methylthiopropanal was added 40 to 90 ppm of hydrogen sulfide, and whether or not there is a corrosive ability was determined. The results are shown in Table 1.

TABLE 1

| Added amount of $H_2S$ (ppm) | Corrosion | Corrosion speed of test piece (mm/y) |
| --- | --- | --- |
| 90 | Corrosion (x) | 1.46 |
| 80 | Corrosion (x) | 1.53 |
| 70 | Corrosion (x) | 1.15 |
| 60 | No corrosion (o) | 0.02 |
| 40 | No corrosion (o) | 0.01 |

Example 2

Evaluation about 3-Mercaptopropanal

To 3-methylthiopropanal was added 3-mercaptopropanal, and whether or not there is a corrosive ability was determined. The results are shown in Table 2. Hydrogen sulfide herein was that contained in 3-mercaptopropanal, and the added amount thereof was converted based on the amount of 3-methylthiopropanal.

TABLE 2

| Added amount of 3-mercaptopropanal (ppm) | Added amount of $H_2S$ (ppm) | Corrosion | Corrosion speed of test piece (mm/y) |
| --- | --- | --- | --- |
| 554 | 2 | Corrosion (x) | 2.02 |
| 533 | 2 | Corrosion (x) | 1.57 |
| 325 | 1 | No corrosion (o) | 0.01 |
| 277 | 2 | No corrosion (o) | 0.02 |

Example 3

Coexistence System of Hydrogen Sulfide and 3-mercaptopropanal

To 3-methylthiopropanal were added hydrogen sulfide and 3-mercaptopropanal, and whether or not there is a corrosive ability was determined. The results are shown in Table 3.

TABLE 3

| Added amount of $H_2S$ (ppm) | Added amount of 3-mercaptopropanal (ppm) | Corrosion | Corrosion speed of test piece (mm/y) |
| --- | --- | --- | --- |
| 23 | 174 | No corrosion (o) | 0.01 |

Example 4

Evaluation about Methyl Mercaptan

To 3-methylthiopropanal was added methyl mercaptan, and whether or not there is a corrosive ability was determined. The results are shown in Table 4.

TABLE 4

| Additive | Added amount (ppm) | Corrosion | Corrosion speed of test piece (mm/y) |
| --- | --- | --- | --- |
| Methyl mercaptan | 1370 | Corrosion (x) | 1.16 |
| Methyl mercaptan | 500 | No corrosion (o) | 0.01 |

As described above, it was found that hydrogen sulfide, 3-mercaptopropanal and methyl mercaptan all had a corrosive ability, and, of these, hydrogen sulfide had higher corrosive ability. In addition, it was also found that when the amount of hydrogen sulfide added was 60 ppm or less and the amount of the thiols added was 500 ppm or less, then the corrosion was extremely inhibited.

Reference Example

To 3-methylthiopropanal was added dimethyl sulfide, pentamethylene sulfide or dimethyl disulfide, and whether or not there is a corrosive ability was determined. The results are shown in Table 5. Corrosion was not confirmed when using these compounds. From these results, sulfides and disulfides are not considered to be included in corrosion-facilitating substances.

TABLE 5

| Additive | Added amount (ppm) | Corrosion | Corrosion speed of test piece (mm/y) |
|---|---|---|---|
| Dimethyl sulfide | 1000 | No corrosion | 0.02 |
| Pentamethylene sulfide | 1000 | No corrosion | 0.01 |
| Dimethyl disulfide | 1450 | No corrosion | 0.01 |

According to the present invention, methionine can be produced while corrosion of a pipe and a reaction vessel are well inhibited in a step of hydrolysis of hydantoin.

What is claimed is:

1. A process for producing a methionine comprising the following steps (1) to (3), wherein the content of thiols in 3-methylthiopropanal is 500 ppm or less, based on the propanal, and the content of hydrogen sulfide in 3-methylthiopropanal is 60 ppm or less, based on the propanal;
   step (1) in which 3-methylthiopropanal is reacted with hydrogen cyanide in the presence of a base to give 2-hydroxy-4-methylthiobutanenitrile;
   step (2) in which the 2-hydroxy-4-methylthiobutanenitrile obtained in step (1) is reacted with ammonium carbonate to give 5-(β-methylmercaptoethyl)hydantoin; and
   step (3) in which the 5-(β-methylmercaptoethy)hydantoin obtained in step (2) is hydrolyzed in the presence of a basic potassium compound to give methionine.

2. The process according to claim 1, wherein the thiols are 3-mercaptopropanal and/or methyl mercaptan.

* * * * *